United States Patent [19]
Heuckeroth et al.

[11] Patent Number: 5,871,954
[45] Date of Patent: Feb. 16, 1999

[54] FATTY ACID ANALOG ENZYME SUBSTRATES

[75] Inventors: Robert O. Heuckeroth, St. Louis; Steven P. Adams, St. Charles; Jeffrey I. Gordon, Olivette, all of Mo.

[73] Assignee: Washington University, St. Louis, Mo.

[21] Appl. No.: 91,550

[22] Filed: Jul. 15, 1993

Related U.S. Application Data

[60] Continuation of Ser. No. 745,660, Aug. 16, 1991, abandoned, which is a division of Ser. No. 208,192, Jun. 16, 1988, abandoned, which is a continuation-in-part of Ser. No. 151,774, Feb. 3, 1988, abandoned.

[51] Int. Cl.⁶ ............................... C12P 21/06; C12P 7/00; C12P 11/00; C12N 9/10
[52] U.S. Cl. .................. 435/68.1; 435/130; 435/132; 435/193; 530/404; 530/406
[58] Field of Search .................................. 435/68.1, 130, 435/132, 193; 530/404, 406

[56] References Cited

U.S. PATENT DOCUMENTS 4,709,012  11/1987  Adams et al. ........................... 530/328
4,740,588   4/1988  Adams et al. ........................... 530/328

OTHER PUBLICATIONS

Chem. Absts. 71: 90840, 1969.
Chem. Absts. 66: 28365, 1967.
Towler et al., Ann. Rev. Biochem., 57, 69–99, (1988).
The Merck Index, Tenth Ed., 1983, p. ONR–96.
Pascal and Ziering, J. Lipid Res. 27, 221–224 (1986).
Heuckeroth et al., J. Biol. Chem. 263(5), 2127–2133 (1988).
Aleynikov et al., Kolsk Branch of the USSR Academy of Sciences, May 3, 1961.
Belov et al., Zhokh, vol. 1, No. 4, D. I. Mendeleev Chemical Engrg. Institute in Moscow, Apr. 18, 1964.
Towler and Glaser, Biochemistry 25, 878–84 (1986).
Towler and Glaser, Proc. Natl. Acad. Sci.USA 83,2812–2816(1986).
Towler et al., Ibid. 84, 2708–2712 (1987).
Towler et al., J. Biol. Chem. 262, 1030–1036 (1987).

*Primary Examiner*—Shailendra Kumar
*Attorney, Agent, or Firm*—Scott J. Meyer

[57] ABSTRACT

Novel oxy- and thio-substituted fatty acid analog substrates of myristoylating enzymes are provided which contain an oxygen or sulfur in place of a methylene group in a carbon position from 4 to 13 in the fatty acid chain of a $C_{13}$–$C_{14}$ fatty acid or alkyl ester thereof.

1 Claim, 1 Drawing Sheet

FATTY ACID ANALOG ENZYME SUBSTRATES

CROSS-REFERENCE TO RELATED APPLICATION

This is a CONTINUATION of application Ser. No. 07/745,660, filed Aug. 16, 1991 now abandoned, which is a Division of application Ser. No. 07/208,192, filed Jun. 16, 1988, now abandoned, which is a continuation-in-part of application Ser. No. 07/151,774, filed Feb. 3, 1988, now abandoned.

This invention was made in part with government support under Grant No. AI 27179, awarded by the National Institutes of Health. The government has certain rights in the invention.

BACKGROUND OF THE INVENTION

This invention relates to novel fatty acid analog substrates of myristoylating enzymes and, more particularly, to oxy- and thio-substituted fatty acid analogs which are useful in the fatty acid acylation of peptides and proteins.

Fatty acid acylation of specific eukaryotic proteins is a well established process which can conveniently be divided into two categories. On the one hand, palmitate ($C_{16}$) is linked to membrane proteins via ester or thioester linkage post-translationally, probably in the Golgi apparatus.

On the other hand, it is known that myristate ($C_{14}$) becomes covalently bound to soluble and membrane proteins via amide linkage early in the protein biosynthetic pathway. In the N-myristoylated proteins, amino-terminal glycine residues are known to be the site of acylation.

A variety of viral and cellular proteins have been shown to be thus modified by the covalent attachment of myristate linked through an amide bound to glycine at their amino termini. An example of a most thoroughly studied myristoylated protein is the transforming protein of Rous sarcoma virus, p $60^{v-src}$.

The myristoylation reaction can be represented as follows:

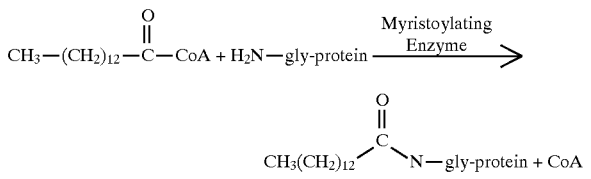

Further background information on the above protein fatty acid acylation can be had by reference to the following series of articles by scientists associated with the Washington University School of Medicine:

Towler and Glaser, *Biochemistry* 25, 878–84 (1986);

Towler and Glaser, *Proc. Natl. Acad. Sci. USA* 83, 2812–2816 (1986);

Towler et al., *Proc. Natl. Acad. Sci. USA* 84, 2708–2712 (1987);

Towler et al., *J. Biol. Chem.* 262, 1030–1036 (1987); and

Towler et al., *Ann. Rev. Biochem.* In Press (1988).

Unique synthetic peptides having relatively short amino acid sequences which are useful as substrates of myristoylating enzymes are described in U.S. Pat. No. 4,740,588. Examples of such peptides are Gly-Asn-Ala-Ala-Ala-Ala-Arg-Arg and
Gly-Asn-Ala-Ala-Ser-Tyr-Arg-Arg.

BRIEF DESCRIPTION OF THE INVENTION

In accordance with the present invention, novel fatty acid analog substrates for myristoylating enzymes are provided. These novel compounds are oxy- and thio-substituted fatty acid analogs which are useful in the fatty acid acylation of proteins. They contain an oxygen or sulfur in place of a methylene (—$CH_2$—) group in a carbon position from 4 to 13 in the fatty acid chain of a $C_{13}$–$C_{14}$ fatty acid or alkyl ester thereof. The carboxyl carbon atom is defined herein as number 1 based on conventional nomenclature. Preferred alkyl esters of the fatty acid analogs have from 1 to 6 carbon atoms in the alkyl group.

These novel substrate compounds are useful for studying the regulation of enzyme action in fatty acid acylation and the role of N-myristoylation in protein function. They can serve as synthetic substrates for the N-myristoylating enzymes in sources such as yeasts, wheat germ lysates and mammmalian cells. These novel compounds differ in hydrophobicity from myristic acid while maintaining approximately the same chain length. Thus, when incorporated into myristoylproteins, they should alter the acylprotein's subsequent interactions with membranes or with hydrophobic proteins. They also have potential use as antiviral and antineoplastic agents.

Illustrative examples of the novel oxy- and thio-substituted fatty acid analog substrate compounds of this invention are:

A. 11-(Ethylthio)undecanoic acid
   $CH_3CH_2S(CH_2)_{10}$ COOH

B. 11-(Ethoxy)undecanoic acid
   $CH_3CH_2O(CH_2)_{10}$ COOH

C. 5-(Octylthio)pentanoic acid
   $CH_3(CH_2)_7S(CH_2)_4$ COOH

D. 11-(Methoxy)undecanoic acid
   $CH_3O(CH_2)_{10}$ COOH

E. 12-(Methoxy)dodecanoic acid
   $CH_3O(CH_2)_{11}$ COOH

F. 5-(octyloxy)pentanoic acid
   $CH_3(CH_2)_7O(CH_2)_4$ COOH

G. 10-(Propylthio)decanoic acid
   $CH_3(CH)_2S(CH_2)_9$ COOH

H. 10-(Propoxy)decanoic acid
   $CH_3(CH_2)_2O(CH_2)_9$ COOH

I. 11-(1-Butoxy)undecanoic acid
   $CH_3(CH_2)_3O(CH_2)_{10}$ COOH

J. 10-(2-Propynoxy)decanoic acid
   $HC{\equiv}CCH_2O(CH_2)_9$ COOH

Alternate nomenclature can be used for the above oxy- and thio-substituted fatty acid analog substrate compounds. For example, compound A can be named 12-thiamyristic acid; compound B can be named 12-oxymyristic acid; and compound J can be named 13-yne-11-oxy-myristic acid.

In a preferred embodiment of the invention the oxy- and thio-substituted fatty acid analog substrate compounds are based on saturated $C_{13}$–$C_{14}$ fatty acids as exemplified by compounds A to H, above.

Compound I, which is a fatty acid analog based on a $C_{16}$ saturated fatty acid, is less effective than the analogs based on $C_{13}$–$C_{14}$ fatty acids.

In still another embodiment, illustrated by compound J, above, the fatty acid analog is based on an ω-unsaturated $C_{14}$ fatty acid. It is believed that results such as obtained with the latter compound also can be achieved with fatty acid analogs based on $\Delta^{9,10}$ cis and $\Delta^{9,10}$ trans unsaturated fatty acids, e.g., 12-thiamyristoleic acid and 12-oxymyristelaidic acid.

The preparation of the oxy- and thio-substituted fatty acid analog substrate compounds can be carried out by methods analogous to the preparation of mixed ethers by the Williamson synthesis. Thus, an appropriate ω-bromo carboxylic acid can be reacted with an alcoholate or an alkyl thiol to produce, respectively, the oxy-substituted fatty acid ether or the thio-substituted fatty acid ether.

In particular, the compounds of the invention can be produced by methods analogous to the synthesis of heteroatom-substituted analogs of stearic acid as described by Pascal and Ziering, *J. Lipid Res.* 27, 221–224 (1986). Using these methods, the sulfur-containing analogs can be prepared by the condensation of appropriate alkyl thiols and ω-bromo carboxylic acids in the presence of alcoholic base. This can be illustrated by the preparation of compound A, above, as follows:

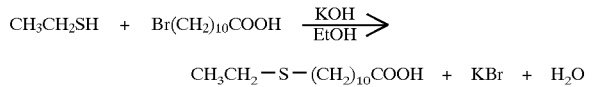

Similarly, the oxygen-containing analogs can be prepared by the reaction of the ω-bromo acids with alcoholic base. This can be illustrated by the preparation of compound E, above, as follows:

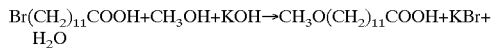

Other oxy- and thio-substituted fatty acid analog substrate compounds of the invention can be prepared by similar such methods by selecting appropriate alkyl and fatty acid chain lengths in the reactant compounds to produce the desired products. Both of the foregoing type reactions are carried out in organic solvent medium at refluxing temperatures until the desired reaction is essentially complete.

Although specific methods of preparation of the novel fatty acid analogs are described herein, it will be understood that the novel compounds of this invention are not limited to any specific method of preparation.

In a typical compound of this invention, namely 11-(ethylthio)undecanoic acid, it has been found that introduction of the thioether moiety into the fatty acid chain unexpectedly and surprisingly decreases its hydrophobicity and the hydrophobicity of the respective acyl peptides and fatty acyl proteins, yet leaves intact its ability to act as a substrate for the enzyme myristoyl CoA: protein N-myristoyl transferase (NMT). Purification and use of this enzyme are described, for example, by Towler et al., *Proc. Natl. Acad. Sci. USA* 84, 2708–2712 (1987); *J. Biol. Chem.* 262, 1030–1036 (1987).

DETAILED DESCRIPTION OF THE INVENTION

Figure 1:
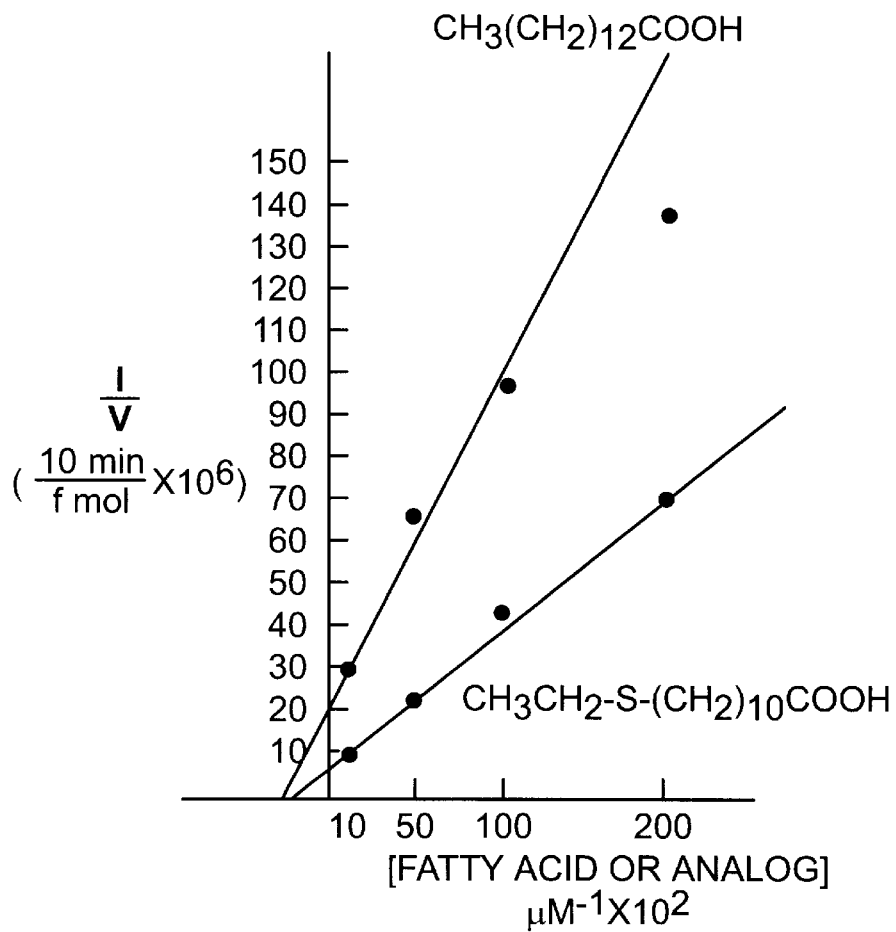

While the specification concludes with claims particularly pointing out and distinctly claiming the subject matter regarded as forming the present invention, it is believed that the invention will be better understood from the following detailed description taken in conjunction with the accompanying drawings in which:

FIG. 1 is a graphical representation which shows a comparison of the kinetic characteristics of myristic acid and 11-(ethylthio)undecanoic acid with wheat germ NMT. Myristoyl CoA and fatty acid analog CoA were generated by incubation of the fatty acid or analog with CoA, ATP and CoA ligase. This reaction mixture was added to wheat germ NMT and Gly-Asn-Ala-Ala-Ser-[$^{125}$I]Tyr-Arg-Arg in the presence of 0.03% Triton® X-100. Reaction products were characterized by reverse phase HPLC and gamma counting.

Figure 2:
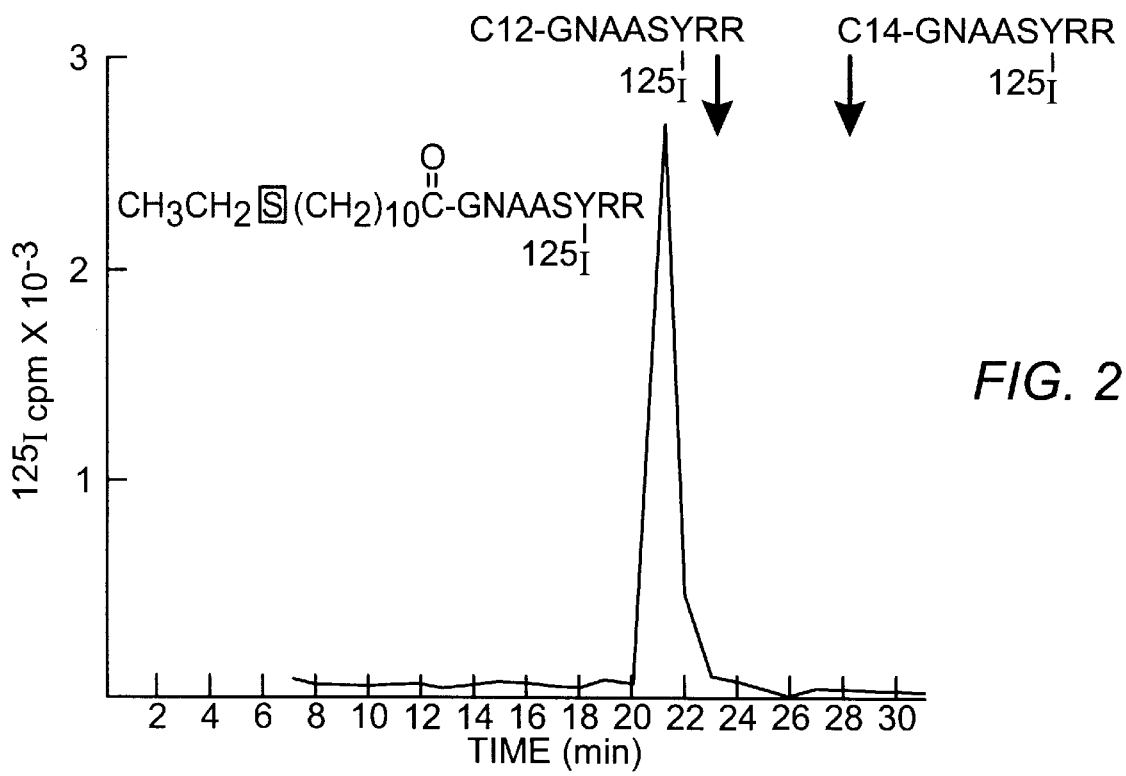

FIG. 2 is a graphical representation which shows the C-18 reverse phase HPLC elution profiles of myristoyl-GNAASYRR[$^{125}$I] and 11-(ethylthio)undecanoyl-GNAASYRR[$^{125}$I]. The fatty acid analog acyl-peptide eluted 7 minutes earlier than the corresponding myristoyl peptide. The free peptide elutes in the void volume (3–5 minutes).

The invention is illustrated in greater detail in the following Examples 1 to 15 by the synthesis and testing of representative compounds of the invention as myristoylating enzyme substrates. Accordingly, the invention is first illustrated in Examples 1 to 5 by the chemical synthesis of a sulfur-containing analog of myristic acid, namely 11-(ethylthio)undecanoic acid, $CH_3CH_2—S—(CH_2)_{10}COOH$, which is then tested in vitro as a wheat germ NMT substrate. Wheat germ NMT is a protein similar to yeast NMT. The purity and chemical identity of the synthesized compound were examined using $^1H$ and $^{13}C$ NMR as well as mass spectroscopy. The assay that was used to characterize the substrate specificity of wheat germ NMT measures the rate of attachment of a radiolabelled fatty acid to an unlabelled peptide. The fatty acid analog synthesized was nonradioactive. The peptide Gly-Asn-Ala-Ala-Ser-Tyr-Arg-Arg was labelled with Na($^{125}$I) in the presence of iodogen. The reaction was chased with cold NaI to create a peptide population uniformly iodinated on Tyr$^6$. Initial tests demonstrated that the fatty acid analog did not significantly alter the kinetic characteristics of the peptide substrate: the $K_m=3$ μM with myristic acid while the $K_m=7$ μM with 11-(ethylthio)-undecanoic acid. The apparent maximal velocity is 2.3 times higher with 11-(ethylthio)-undecanoic acid than with myristic acid. The iodinated peptide was used at saturating concentrations for all further tests (40 μM).

The CoA (Coenzyme A) ester of the sulfur-containing analog appeared to be at least as good a substrate for wheat germ NMT as myristoyl CoA itself. FIG. 1 shows representative data from one of three tests comparing the kinetic characteristics of myristate and the sulfur containing analog with wheat germ NMT. The $K_m$ for the analog is 1.5 times higher than for myristate, while the $V_{max}$ for the analog is 3.5 times higher. This difference in $K_m$ and $V_{max}$ between analog and myristate was noted in each test. The in vitro assay for NMT activity requires the enzymatic generation of fatty acyl CoA. Since the *Pseudomonas* acyl CoA ligase is quite nonspecific [Shimizo et al., *Anal. Biochem.* 107, 193–198 (1980)] and is used in excess, it should equally well convert myristic acid and 11-(ethylthio)undecanoic acid to the corresponding CoA esters. It is, therefore, believed that the data represent the relative catalytic efficiency of fatty acyl CoA and analog CoA for wheat germ NMT.

Similar results were obtained using an 11,000-fold purified preparation of yeast NMT [Towler et al., *Proc. Natl. Acad. Sci. USA* 84, 2708–2712 (1987)]. The $K_m$ and $V_{max}$ for the analog was indistinguishable from that of the C14:0 fatty acid.

11-(ethylthio)undecanoic acid has another interesting characteristic which is believed to be useful for studying the biological role of protein N-myristoylation—namely its hydrophobicity is significantly different from that of myristic acid. This difference was evident when the HPLC elution characteristics of fatty acyl peptides were examined. The elution time of a particular acyl-peptide depends strongly on the peptide sequence as well as on the acyl chain attached to that peptide. For example, the elution times of fatty acyl derivatives of GNAAAARR are (in minutes) decanoic acid, 9; dodecanoic acid, 18; myristic acid, 24; and palmitic acid, 30. Elution times for fatty acyl derivatives of GNAAS[$^{125}$I] YRR are 23 and 28 minutes for C12 and C14 fatty acids, respectively (FIG. 2). 11-(ethylthio)undecanoyl-GNAAS [$^{125}$I]YRR eluted seven minutes earlier than the corresponding myristoyl-peptide (FIG. 2). This suggests that the substitution of a sulfur for a carbon in the backbone of the fatty acid chain (at least at position 12) has an effect similar to shortening the chain length of the fatty acid by two carbons. Such a change could alter the biological activity of myristoyl proteins.

EXAMPLE 1

Synthesis of 11-(ethylthio)undecanoic Acid

11-Bromoundecanoic acid (1 g, 3.77 mmol, Aldrich) was added to a solution of ethanethiol (0.279 mL, 3.77 mmol, Aldrich) and potassium hydroxide (0.486 g, 8.66 mmol) in absolute ethanol (40 mL) and refluxed for 5 hr under a nitrogen atmosphere. After cooling and acidification with HCl, solvent was removed under reduced pressure to give a white solid. The solid was dissolved in ethyl acetate and extracted with water. The organic phase was dried over sodium sulfate, filtered and the solvent removed under reduced pressure. The product was purified by silica column chromatography using increasing concentrations of ethyl acetate in hexane for elution. The product eluted at 25% ethyl acetate/hexane. Solvent was removed under reduced pressure to yield 11-(ethylthio)-undecanoic acid (76 mg, 8%), mp 58°–61° C.; $^1$H NMR (300 MHz, CDCl$_3$) δ 1.24 (t, 3H, J=7.4, CH$_3$), 1.20–1.40 (bm, 12H, methylene envelope), 1.48–1.67 (bm, 4H, S—CH$_2$—CH$_2$ COO—CH$_2$—CH$_2$), 2.33 (t, 2H, J=7.5, CH$_2$—COOH), 2.49 (t, 2H, J=7.4, S—CH$_2$—CH$_2$), 2.51 (q, 2H, J=7.4, S—CH$_2$—CH$_3$), 10.5 (br, 1H, COOH); $^{13}$C NMR (75.4 MHz, CDCl$_3$) δ 14.88, 24.70, 25.98, 28.97, 29.08, 29.24*, 29.38, 29.48, 29.69, 31.73, 34.11, 180.05; MS, m/z 246 (M$^+$, 50), 217 (COOH (CH$_2$)$_{10}$S$^+$, 7), 199 (100), 181 (7), 167 (7), 149 (6), 117 (7), 101 (9), 97 (9), 87 (14), 83 (18), 75 (54), 69 (29), 62 (18), 55 (37).

EXAMPLE 2

Preparation of Gly-Asn-Ala-Ala-Ser-[$^{125}$I]-Tyr-Arg-Arg

In a typical test, 100 μL of a 2 mg/ml stock (approximately 2 mM) of the peptide Gly-Asn-Ala-Ala-Ser-Tyr-Arg-Arg, was adjusted to pH 7.4 with NaOH and diluted to 0.5 mL with PBS (30 mM sodium phosphate, pH 7.5, 150 mM NaCl). This solution was added to an iodogen (Pierce) coated polypropylene tube and incubated with carrier free Na$^{125}$I (400 μCi) for 15 minutes at room temperature. Cold NaI was then added to a final concentration of 2 mM and incubation was allowed to proceed for another 15 minutes. The reaction mixture was loaded onto a disposable octadecyl (C$_{18}$) column (Baker) which had been pre-equilibrated with 0.05% trifloroacetic acid in water. Na$^{125}$I was removed by washing the column with 10 volumes of 0.05% trifloroacetic acid/water. Peptide was then eluted with 25% acetonitrile/ 0.05% trifloroacetic/water, and the solvent removed under a stream of nitrogen. The iodinated peptide was resuspended in water at a final concentration of 2 mg/ml. Peptide specific activity was 100,000 cpm/nmol.

EXAMPLE 3

Partial Purification of NMT from Wheat Germ

Procedures developed earlier by Towler et al., *J. Biol. Chem.* 262, 1030–1036 (1987), for yeast NMT were employed for wheat germ NMT purification with slight modifications. All steps were carried out at 4° C. unless otherwise indicated. Protein was quantitated by the method of Bradford, *Anal. Biochem.* 72, 248–254 (1986). NMT activity was assayed as described by Towler and Glaser, *Biochemistry* 25, 878–884 (1976), using a synthetic peptide Gly-Ser-Ser-Lys-Ser-Lys-Pro-Lys, derived from the N-terminal sequence of p60$^{v-src}$. This peptide was used because of its greater stability in crude enzyme fractions compared to other peptide substrates. Seven hundred and fifty mL of buffer A (20 mM N-2-hydroxyethylpiperazine-N'-2-ethanesulfonic acid, pH 7.6, 100 mM potassium acetate, 1 mM magnesium acetate, 2 mM calcium chloride, 1 mM DTT) prechilled to 4° C. was added to 300 g of untoasted wheat germ. The slurry was homogenized in a Waring blender for 15 seconds. The sample was then centrifuged at 27,500×g for 20 minutes. The resulting supernatant was filtered through cheesecloth and concentrated overnight in an Amicon concentrator with a YM30 membrane. N-2-hydroxyethylpiperazine-N'-2-ethanesulfonic acid (pH 7.6) was added to a final concentration of 0.1 M. Sequential ammonium sulfate fractionation was carried out as described by Towler et al., *J. Biol. Chem.* 262, 1030–1036 (1987). After resuspending the 25–50% fraction in buffer B (50 mM Tris HCl, pH 7.4, 1 mM DTT, 0.1 mM EGTA, 1 μg/mL each of the peptide protease inhibitors aprotinin, soybean trypsin inhibitor, leupeptin and pepstatin) the sample was dialyzed against three changes of buffer B (4 L per exchange). The sample was then diluted 4-fold and centrifuged for 10 minutes at 11,750×g. An aliquot of the supernatant (90 ml of 420 ml) was loaded (at 200 mL/hr) onto a 5 ×23-cm DEAE-Sepharose® CL-6B column (Pharmacia P-L Biochemicals) preequilibrated with buffer C (20 mM Tris HCl, pH 8, 1 mM DTT). The column was successively washed with one column volume of buffer C plus 0, 50, 100, or 200 mM NaCl. Material with the highest specific activity eluted in the 100 mM NaCl wash (fractions 59–72) and was used for further purification. After concentrating to ~40 mL with a YN30 membrane, this fraction was dialyzed (2×2 L) against buffer D (10 mM Tris HCl, pH 7.4, 1 mM DTT, 0.1 mM EGTA), plus the peptide protease inhibitors listed above. It was subsequently added to a 5 mL slurry of Type V AG-CoA (CoA-agarose affinity matrix; Pharmacia P-L Biochemicals) pre-equilibrated with buffer D plus protease inhibitors. After 5 hrs of continuous mixing, the suspension was poured into a 2.5 cm high×1.5 cm diameter column and washed with three column volumes of buffer D. This was followed by sequential step elutions with 100, 200 or 500 mM KCl in buffer D (3 column volumes each). NMT activity eluted in the 200 and 500 mM KCl washes. These fractions were combined, dialyzed against buffer E (10 mM potassium phosphate, pH 7.4, 1 mM DTT) and loaded onto a Bio-Gel HTP column (5 g of hydroxylapatite; Bio-Rad) as described by Towler et al., *J. Biol. Chem.* 262, 1030–1060 (1987). NMT activity was eluted with 200 mM potassium phosphate. This fraction was concentrated and dialyzed with buffer D using Centricon-30 microconcentrators (Amicon). Partially purified NMT was stored at 4° C. as a 77 mg/mL protein solution and used, after appropriate dilution, for all further characterization. (DTT=DL-dithiothreitol; EGTA= ethyleneglycol-bis-(β-aminoethylether)—N,N,N',N'-tetraacetic acid.)

The purification results are set forth in the following table.

TABLE 1

Partial Purification of Wheat Germ NMT

| Fraction | Volume[a] (mL) | Protein Concentration (mg/mL) | Specific Activity (units[b]/mg) | Fold Purification | % Yield |
|---|---|---|---|---|---|
| Initial Extract | 60 | 126 | 0.67 | 1 | 100 |
| 25–50% Ammonium Sulfate Fraction | 90 | 32 | 4.2 | 6.3 | 239 |
| DEAE Column | 39 | 8 | 17.5 | 26 | 108 |
| CoA Column | 21 | 0.71 | 293 | 437 | 86 |
| Hydroxyapatite Column | 0.087 | 77 | 323 | 480 | 43 |

[a]Volumes of the initial extract and ammonium sulfate fraction listed in this Table are 20% of the actual volumes used at these stages of purification since only 20% of the sample was used for subsequent purification steps.
[b]One unit of activity is defined as 1 pmol acylpeptide formed/min.

EXAMPLE 4

Characterization of Partially Purified Wheat Germ NMT

Assays for NMT activity were performed using a procedure detailed previously by Towler and Glaser, *Proc. Natl. Acad. Sci. USA* 83, 2812–2816 (1986). Briefly, the in vitro assay measures the transfer of radiolabelled fatty acid from acyl CoA to a synthetic peptide substrate. The acylpeptide product is identified by reverse phase HPLC. Time and enzyme dependence were evaluated by varying the reaction time or the enzyme concentration. A 10 minute reaction time was found to be in the linear range for product formation (data not shown). Fatty acid specificity was examined essentially as described by Towler et al., *J. Biol. Chem.* 262, 1030–1036 (1987), except that the peptide Gly-Ser-Ser-Lys-Ser-Lys-Pro-Lys rather than Gly-Asn-Ala-Ala-Ala-Ala-Arg-Arg was used to compare palmitate and myristate utilization by wheat germ NMT. This was necessary because of the presence of a large, peptide-independent peak which co-eluted with a palmitoyl-Gly-Asn-Ala-Ala-Ala-Ala-Arg-Arg standard. [$^3$H]Palmitate and [$^3$H]myristate were used in this comparison. [$^{14}$C]fatty acids were used to compare C-10, C-12 and C-14 chain lengths. Fatty acyl CoA concentrations in these assays were determined by a modification of the method of Hosaka et al., *Methods Enzymol.* 71, 325–333 (1981).

EXAMPLE 5

Characterization of the Fatty Acid Analog

Gly-Asn-Ala-Ala-Ser-[$^{125}$I]Tyr-Arg-Arg as prepared in Example 2, above, was tested in an in vitro myristoylation system which was modified from that used with radiolabelled fatty acids. To determine the $K_m$ of the peptide with myristic acid and the thioether analog as substrates, cold myristate and 11-(ethylthio)undecanoic acid were used in the acyl CoA generating system [Towler et al., *J. Biol. Chem.* 262, 1030–1036 (1987); Towler and Glaser, *Proc. Natl. Acad. Sci. USA* 83, 2812–2816 (1986)] at a final concentration of 5 μM. 20-fold more wheat germ NMT (480-fold purified as in Example 3, above) was used for these assays than for assays which employed [$^3$H] myristate. This amount of NMT was found to be in the linear range of enzyme concentration (data not shown). Double reciprocal plots were generated for the iodinated peptide with both myristic acid and the sulfur analog by altering the peptide concentration in the presence of a constant amount of fatty acid or analog. For determination of the Km of 11-(ethylthio)undecanoic acid and cold myristic as their CoA esters, saturating concentrations of iodinated peptide (40 μM) were used and the level of fatty acid or analog was varied. The assays contained 0.03% Triton X-100 to maintain the solubility of the fatty acids. The results are shown in FIG. 1.

Other illustrative examples of the oxy- and thio-substituted fatty acid analog substrate compounds of the invention were synthesized in Examples 6 to 14 and tested in Example 15 as substrates for the yeast NMT. A comparison of the kinetic characteristics of these analog substrates using myristic acid as a standard is set forth in the Table 2.

For these Examples, each analog synthesized is characterized by $^1$H and 13C NMR as well as mass spectroscopy. The analogs are then characterized kinetically as NMT substrates. Briefly, fatty acid analogs are converted to their CoA esters with Pseudomonas CoA ligase and incubated with the iodinated peptide GNAAS[$^{125}$I]YRR and a source of NMT. Peptide $K_m$ and $V_m$ are first determined by varying peptide concentration with fatty acid analog at 15 μM (generally a saturating concentration). The radiolabelled peptide is then used at concentrations which will lead to 50% enzyme saturation (i.e., at its $K_m$) for the determination of fatty acid analog kinetic characteristics. Representative analogs with sulfur or oxygen in the backbone of the fatty acid chain serve as good substrates for NMT in vitro and will compete for incorporation of $^3$H labelled myri-state into yeast proteins in vivo. In addition, these analogs differ markedly in hydrophobicity from myri-state as measured both by $C_{18}$ reverse phase HPLC elution profiles and by 2-octanol/water partition coefficients. The analog $CH_3O(CH_2)_{11}COOH$, for example, partitions into water 20 fold better than myristate. It is believed that these analogs will be incorporated into mammalian acylproteins in vivo and that their incorporation into these proteins will drastically alter protein processing or targeting. It is further believed that the incorporation of fatty acid analogs of both myristate and palmitate into ester linked and phosphatidyl inositol glycan linked acylproteins will also dramatically alter their properties. Since many viral proteins and oncogenes are acylated, these compounds represent a new class of potential antiviral and antineoplastic agents.

EXAMPLE 6

Synthesis of 11-(ethoxy)undecanoic acid 11-bromoundecanoic acid (2.25 g, 8.47 mmol) was added to a solution of potassium hydroxide (2.15 g, 38.3 mmol) in absolute ethanol (20 mL) and refluxed for 7 hrs. After cooling and acidification with HCl, solvent was removed under reduced pressure to give a white solid. The sample was dissolved in ethyl acetate and extracted with water. The organic phase was dried over sodium sulfate, and the solvent was removed under reduced pressure. The product was purified by silica column chromatography in 1% diethyl ether/0.3% formic acid/methylene chloride. Solvent was removed under reduced pressure to yield 11-(ethoxy)undecanoic acid (680 mg, 35%): mp 44°–45.5° C.; $^1$H NMR (300 MHz, CDCl$_3$) δ 1.20 (t, 3H, J=7.0, CH$_3$), 1.24–1.40 (bm, 12H, methylene envelope), 1.52–1.68 (bm, 4H, O—CH$_2$—CH$_2$; CH$_2$—CH$_2$—COOH), 2.34 (t, 2H, J=7.5, CH$_2$—COOH), 3.41 (t, 2H, J=6.8, O—CH$_2$—CH$_2$), 3.48 (g, 2H, J=7.0, 0—CH$_2$—CH$_3$), 10.25 (br, 1H, COOH); $^{13}$C NMR (75.4 MHz, CDCL$_3$) δ 15.27, 24.75, 26.23, 29.11, 29.26, 29.40, 29.55*, 29.80, 34.12, 66.06, 70.76, 179.71; m/z 231 (M+H$^+$).

EXAMPLE 7

A. Synthesis of Methyl 6-thiotetradecanoate n-Butyllithium (8.3 mL, 22.1 mmol) was added dropwise to a solution of octanethiol (1; 2.9 g, 19.8 mmol) in dry THF (198 mL) at 0° C. After stirring at 0° C. for 30 min, a solution of methyl 5-bromopentanoate (2; 4.2 g, 21.6 mmol) in dry THF (43 mL) was added dropwise and the resulting heterogeneous mixture was stirred overnight at room temperature. The mixture was concentrated and the residue was partitioned between ether and saturated $NH_4Cl$. After extracting the aqueous layer a second time with ether, the combined organic extracts were washed with brine, dried ($MgSO_4$) and concentrated. Purification by reduced pressure distillation (140°–145° C. at 2 mmol) afforded 4.4 g (86%) of the title product. $^1$H-NMR data, δ 3.63 (s, 3H, $OCH_3$); 2.48 (q, 4H, J=6.8 Hz, $CH_2$—S—$CH_2$); 2.30 (t, J-7.0 Hz, $CH_2CO_2CH_3$); 1.78–1.48 (bm, 6H, $CH_2$'s beta to thio and ester moieties); 1.43–1.15 (bs, 10H, $CH_2$'s); 0.85 (t, J=6.6 Hz, CH3); $^{13}$C-NMR data: δ 173.7, 51.4, 33.5, 32.1, 31.7, 31.6, 29.6, 29.1 (2), 29.0, 28.8, 24.1, 22.5, 14.0.

B. Synthesis of 5-(Octylthio)pentanoic acid

NaOH (1.24 g, 31.0 mmol) was added to a solution of methyl 6-thiotetradecanoate (4.25 g, 16.3 mmol) in dry methanol (55 mL) and the resulting mixture brought to reflux. After 5 h the reaction was cooled to room temperature, diluted with 100 ml of water and acidified with 1 M HCl to a pH of 3. This acidified solution was extracted with ether (2X) and the combined organic extracts were washed in water (2X), brine (2X), dried ($MgSO_4$) and concentrated. Column chromatography (ethyl acetate-pentane, 1:9) of the residue afforded 1.4 g, 35% of product. $^1$H-NMR data, δ 2.46 (q, 4H, J=7.6 Hz, $CH_2SCH_2$); 2.33 (t, 2H, J=7.2 Hz, $CH_2CO_2H$); 1.75–1.45 (bm, 6H, $CH_2$'s beta to thio and acid moieties); 1.38–1.15 (bs, 10H, $CH_2$'s); 0.83 (t, 3H, J=6.6 Hz, $CH_3$); $^{13}$C-NMR data, 179.4, 33.5, 32.1, 31.8, 31.6, 29.7, 29.1 (2), 28.9 (2), 23.8, 22.6, 14.0; m/z (E1): 246, 145 (100%), 115, 101, 88, 69.

EXAMPLE 8

Synthesis of 11-(methoxy)undecanoic acid

11bromoundecanoic acid (10.0 g, 37.7 mmol) was added to a solution of potassium hydroxide (24.3 g, 433 mmol) in methanol (280 mL) and refluxed for 5 hrs. After cooling and acidification with HCl, solvent was removed under reduced pressure. The sample was dissolved in ethyl acetate and extracted with water. The organic phase was dried over sodium sulfate, and the solvent removed under reduced pressure. The product was purified by silica column chromatography using increasing concentrations of ethyl acetate in hexanes for elution. The product eluted in 25% ethyl acetate in hexanes. Solvent was removed under reduced pressure to give 11-(methoxy)undecanoic acid (200 mg, 2.5%): mp 31°–32° C.; $^1$H NMR (300 MHz, $CDCl_3$) δ 1.1–1.3 (bm, 12H, methylene envelope), 1.45–1.63 (bm, 4H, O—$CH_2$—$CH_2$, $CH_2$—$CH_2$—COOH), 2.34 (t, 2H, J=7.3, $CH_2$—COOH), 3.45 (s, 3H, $CH_3$), 3.50 (t, 2H, J=6.8, O—$CH_2$), 10.70 (br, COOH); $^{13}$C NMR (75.4 MHz, $CDCl_3$) δ 24.64, 26.00, 29.00, 29.16, 29.29, 29.40, 34.00, 58.23, 72.81, 179.17; m/z 216 ($M^+$).

EXAMPLE 9

Synthesis of 12-(methoxy)dodecanoic acid 12-bromododecanoic acid (2.0 g, 7.16 mmol) was added to a solution of potassium hydroxide (1.61 g, 28.65 mmol) in methanol (30 mLs) and refluxed for 20 hrs. After cooling and acidification with HCl, solvent was removed under reduced pressure. The sample was dissolved in ethyl acetate and extracted with water. The organic phase was dried over sodium sulfate, and the solvent removed under reduced pressure. The product was purified by silica column chromatography in 1% diethyl ether/0.3% formic acid/methylene chloride to yield 12-(methoxy)dodecanoic acid (640 mg, 39%): mp 45°–47° C.; $^1$H NMR (300 MHz, $CDCl_3$) δ 1.20–1.45 (bm, 15H, methylene envelope), 1.51–1.69 (bm, 4H, O—$CH_2$—$CH_2$, $CH_2$—$CH_2$—COOH), 2.34 (t, 2H, J=7.4, $CH_2$—COOH), 3.34 (s, 3H, O—$CH_3$), 3.38 (t, 2H, J=6.7, O—$CH_2$), 10.99 (br, 1H, COOH); $^{13}$C NMR (75.4 MHz, $CDCl_3$) δ 24.75, 26.16, 29.10, 29.27, 29.38, 29.44, 29.53, 34.12, 58.50, 72.97, 179.70; m/z 231 ($M+H^+$).

EXAMPLE 10

Synthesis of 5-(octyloxy)pentanoic acid 5-bromopentanoic acid (2g, 11.0 mmol) was added to a solution of potassium hydroxide (2.48 g, 44.2 mmol) in 1-octanol (20 mL) and stirred at 97° C. for 27 hrs. After cooling, the product was extracted at pH=1 with ethyl acetate and water. The organic phase was dried over sodium sulfate and solvent was removed. 1-octanol was removed by short path (Kugelrohr) distillation (50°–70° C., 0.5 mm Hg). To ensure complete cleavage of the octyl ester, the residue was stirred 3 hrs with methanol/water/KOH (50%/50%/2.5 g, 40 mL) at 25° C. 1-octanol was extracted into ethyl acetate at pH=12. 5-(octyloxy)pentanoic acid was extracted from the aqueous phase into ethyl acetate after adjusting the pH to 1.5 with HCl. After drying over sodium sulfate, the solvent was removed at reduced pressure. Silica column chromatography in 10% ethyl acetate/hexane/0.3% formic acid, yielded 5-(octyloxy)pentanoic acid (235 mg, 9%): mp<30° C.; $^1$H NMR (300 MHz, $CDCl_3$) δ 0.88 (t, 3H, J=6.6), 1.18–1.39 (bm, 10H, methylene envelope), 1.48–1.77 (bm, 6H, $CH_2CH_2OCH_2CH_2$, $CH_2CH_2COOH$), 2.39 (t, 2H, J=7.1, $CH_2COOH$), 3.34-3.49 (bm, 4H, $CH_2OCH_2$), 10.66 (br, 1H, COOH); $^{13}$C NMR (75.4 MHz, $CDCl_3$) 14.18, 21.59, 22.73, 26.22, 29.03, 29.32, 29.51, 29.72, 31.89, 33.85, 70.22, 71.07, 179.55; m/z 231 (M+H).

EXAMPLE 11

Synthesis of 10-(propylthio)decanoic acid 10-bromodecanoic acid (1.0 g, 3.98 mmol) was added to a solution of potassium hydroxide (0.893 g, 15.9 mmol) in 1-propanethiol (30 mL) and methanol (30 mL) and stirred at 69° C. for 18 hrs. The reaction was allowed to cool to room temperature after the addition of 20 mL water. After acidification to pH=1 and extraction into ethyl acetate, the organic phase was dried over sodium sulfate and solvent removed at reduced pressure to yield a white crystalline powder. The product was purified by silica column chromatography in 8% ethyl acetate/hexane/0.3% formic acid and recrystallization from hexane to yield 10-(propylthio) decanoic acid (210 mg, 21%), mp 42°–43.5° C.; $^1$H NMR (300 MHz, $CDCl_3$) δ0.96 (t, 3H, J=7.3, $CH_3$) 1.15–1.40 (bm, 10H, methylene envelope), 1.49–1.64 (bm, 6H, $CH_3CH_2CH_2SCH_2CH_2$, $CH_2CH_2COOH$), 2.32 (t, 2H, J=7.6, $CH_2COOH$), 2.40-2.55 (bm, 4H, $CH_3CH_2CH_2SCH_2$), 10.93 (Br, 1H, COOH); $^{13}$C NMR (75.4 MHz, $CDCL_3$) δ 13.64, 23.09, 24.71, 28.96, 29.07, 29.13, 29.24, 29.36, 29.77, 32.16, 34.10, 34.28, 179.98; m/z 247 (M+H).

EXAMPLE 12

Synthesis of 10-(propoxy)decanoic acid 10-bromodecanoic acid (1 g, 3.98 mmol) was added to a solution of potassium hydroxide (0.893 g, 15.9 mmol) in n-propanol (30 mL) and stirred at 102° C. for 18 hrs. The reaction was allowed to cool to room temperature after the addition of 20 mL water. After acidification to pH=1 and extraction into ethyl acetate, the organic phase was dried over sodium sulfate and solvent removed at reduced pressure to yield a yellow oil. The product was purified by silica column chromatography in 2% diethyl ether/methylene chloride/0.2% formic acid, and then in 7% ethyl acetate/hexane/0.3% formic acid. Recrystallization from hexane at −20° C. yielded 10-(propoxy)decanoic acid (74 mg, 12%): mp <30° C.; $^1$H NMR (300 MHz, CDCl$_3$) δ 0.91 (t, 3H, J=7.5, CH$_3$), 1.18–1.40 (br, 10H, methylene envelope), 1.48–1.67 (bm, 6H, CH$_3$CH$_2$CH$_2$OCH$_2$CH$_2$, CH$_2$CH$_2$COOH), 2.33 (t, 2H, J=7.4, CH$_2$COOH), 3.31–3.45 (bm, 4H, CH$_2$OCH$_2$), 10.37 (br, 1H COOH); $^{13}$C NMR (75.4 MHz, CDCl$_3$) 10.67, 22.94, 24.72, 26.19, 29.09, 29.22, 29.41, 29.74, 34.11, 70.88, 72.53, 179.69; m/z 231 (M+H).

EXAMPLE 13

Synthesis of 11-(1-butoxy)undecanoic acid 11-bromoundecanoic acid (2 g, 17.5 mmol) was added to a solution of potassium hydroxide (1.7 g, 30.2 mmol) in 1-butanol (20 mL) and the solution was stirred at 40° C. for 5 hrs. After cooling, the reaction mixture was extracted with ethyl acetate and water at pH=2. The organic phase was then washed with saturated sodium chloride, dried over sodium sulfate, and the solvent was removed under reduced pressure. The product was purified over silica column chromatography in 2–10% ethyl acetate/hexane/0.2% formic acid to yield 11-(1-butoxy)undecanoic acid (336 mg, 17%). mp 29°–30.5° C.; $^1$H NMR (300 MHz, CDCl$_3$) δ 0.84–0.96 (t, 3H, J=7.3, CH$_3$), 1.18–1.46 (bm, 14H, methylene envelope), 1.47–1.68 (bm, 6H, CH$_2$CH$_2$OCH$_2$CH$_2$, CH$_2$CH$_2$COOH), 2.31 (t, 2H, CH$_2$COOH), 3.32–3.46 (bm, 4H, CH$_2$OCH$_2$), 11.02 (br, 1H, COOH); $^{13}$C NMR (75.4 MHz, CDCl$_3$ δ 14.02, 19.43, 24.74, 26.21, 29.11, 29.28, 29.35, 29.56, 29.64, 29.76, 31.85, 34.14, 70.63, 70.94, 179.82; m/z 259 (M+H).

EXAMPLE 14

Synthesis of 10-(2-propynoxy)decanoic acid

Sodium hydride (420 mg, 8.75 mmol) was added to propargyl alcohol (68 mL, 1.17 mol) at 4° C. and stirred for 30 minutes at 25° C. 10-Bromedecanoic acid (2 g, 7.96 mmol) was added to this mixture and the reaction was stirred at 98° C. for 48 hrs. The reaction mixture was extracted with water and ethyl acetate at pH=0. After drying the organic phase over sodium sulfate, the solvent was removed at reduced pressure. Product was purified over silica gel chromatography in 7–10% ethyl acetate/hexane/0.3% formic acid and then over a second silica gel column in 1–2.5% ethyl acetate/benzene/0.3% formic acid to yield 10-(2-propynoxy)decanoic acid (245 mg, 14%). mp <30° C.; $^1$H NMR (300 MHz, CDCl$_3$) δ 1.25–1.42 (br, 10H, methylene envelope), 1.54–1.70 (bm, 4H, OCH$_2$CH$_2$, CH$_2$CH$_2$COOH), 2.35 (t, 2H, J=7.4, CH$_2$COOH), 2.43 (t, 1H, J=2.3, HC≡C), 3.52 (t, 2H, J=6.8, OCH$_2$), 4.14 (d, 2H, J=2.5, C≡CCH$_2$O), 10.42 (br, 1H, COOH); $^{13}$C NMR (75.4 MHz, CDCl$_3$) δ 24.68, 26.06, 29.04, 29.17, 29.35*, 29.46, 34.09, 57.95, 70.22, 74.09, 79.90, 180.02; m/z 227 (M+H).

EXAMPLE 15

A. Labeling and Extraction of Yeast Proteins

Saccharomyces cerevisiae strain BJ405 [MATα, trpl, prbl, prcl, pep4-3; Hemmings et al., Proc. Natl. Acad. Sci. USA 78, 435–439 (1981)] (previously referred to as JR153) was grown to mid-log phase (OD$_{660nm}$=1.0–1.2) in YPD medium (1% yeast extract/2% Bactopeptone/2% Dextrose) at 30° C. in a rotary shaker water bath. Cells were pretreated with Cerulenin at 2 μg/ml for 15 minutes and then incubated for 20–45 minutes with unlabeled myristate, palmitate or fatty acid analog at 100 μM in the presence of either 5 μM [9,10-$^3$H(N)]-myristate (22.4 Ci/mmol) or L-[$^{35}$S] methionine (1106 Ci/mmol) at 30 μCi/ml of culture.

Cells were cooled on ice 5 minutes, pelleted at 10,000×g, then broken and extracted by the method of Towler et al., Proc. Natl. Acad. Sci. USA 83, 2812–2816 (1986). Total protein synthesis was assayed by trichloroacetic acid (TCA) precipitation. Proteins were separated by SDS-12% polyacrylamide gel electrophoresis, and [$^3$H]fatty acid incorporation into cellular acyl-proteins was assayed by autoradiography followed by laser densitometry.

B. Results

Incubation of cells with the 12-(methoxy)dodecanoic acid analog resulted in a 35–60% reduction in the incorporation of [$^3$H]myristate into a known yeast myristoylprotein of M$_r$ 20 kDa [Towler et al, PNAS 83, 2812–2816 (1986)] compared to control cells which were incubated either with [$^3$H]myristate alone (i.e. no analog) or 100 μM palmitate. By contrast, addition of [$^3$H]myristate and 100 μM myristate results in a 75–80% reduction in the incorporation of [$^3$H] myristate into this cellular acylprotein.

The analog does not appear to be toxic to cells. No difference in the growth rates were observed between cells treated with 100 μM myristate and 100 μM analog. Furthermore, 100 μM myristate and 100 μM analog produced a similar modest reduction (10–15%) in total protein synthesis (measured by the incorporation of [$^{35}$S]methionine into TCA precipitable protein) compared to control cells which were not exposed to exogenous fatty acid.

Together these results indicate that the analog can successfully enter yeast and compete with labeled myristate for incorporation into a known myristoylprotein.

TABLE 2

Kinetics of Fatty Acid Analogs

| Analog | Elution Time (min.) | Peptide $K_m$ μM | Peptide $V_m$ | Acyl CoA $K_m$ μM | Acyl CoA $V_m$ |
|---|---|---|---|---|---|
| CH$_3$(CH$_2$)$_{12}$COOH* | 26 | 10 | 100% | 0.6 | 100% |
| CH$_3$CH$_2$S(CH$_2$)$_{10}$COOH | 18 | 19 | 98% | 1.4 | 130% |
| CH$_3$CH$_2$O(CH$_2$)$_{10}$COOH | 12 | 14.8 | 62% | 1.8 | 64% |
| CH$_3$(CH$_2$)$_7$S(CH$_2$)$_4$COOH | 21 | 11.5 | 213% | 1.5 | 160% |
| CH$_3$O(CH$_2$)$_{10}$COOH | 12–13 | 47.3 | 232% | 6.9 | 163% |
| CH$_3$O(CH$_2$)$_{11}$COOH | 12–13 | 19.1 | 177% | ~2 | ~110% |
| CH$_3$(CH$_2$)$_7$O(CH$_2$)$_4$COOH | 16 | 31 | 335% | 1.6 | 675% |
| CH$_3$(CH$_2$)$_2$S(CH$_2$)$_9$COOH | 18 | 47 | 245% | 1.5 | 250% |
| CH$_3$(CH$_2$)$_2$O(CH$_2$)$_9$COOH | 11–12 | 34 | 150% | 6.1 | 250% |
| CH$_3$(CH$_2$)$_3$O(CH$_2$)$_{10}$COOH | 19 | 42 | 25% | 1 | 80% |
| HC≡CCH$_2$O(CH$_2$)$_9$COOH | 9 | 28 | 200% | 6.5 | 320% |

*Myristate control

It will be seen that the $K_m$ for each of the analogs is higher than for myristate, while the $V_{max}$ for the analogs is higher in most cases.

Standard amino acid abbreviations are used to identify the sequence of the peptides herein as follows:

| Amino Acid | Abbreviation |
| --- | --- |
| L-Alanine | Ala or A |
| L-Arginine | Arg or R |
| L-Asparagine | Asn or N |
| L-Aspartic acid | Asp or D |
| L-Glutamine | Gln or Q |
| L-Glycine | Gly or G |
| L-Leucine | Leu or L |
| L-Lysine | Lys or K |
| L-Proline | Pro or P |
| L-Serine | Ser or S |
| L-Tyrosine | Tyr or Y |
| L-Valine | Val or V |

Various other examples will be apparent to the person skilled in the art after reading the present disclosure without departing from the spirit and scope of the invention. All such other examples are included within the scope of the appended claims.

What is claimed is:

1. A method of acylating a peptide or protein comprising reacting the CoA ester of an oxy- or thio-substituted fatty acid analog compound having activity as a substrate of myristoylating enzymes selected from the group consisting of $C_{13}$ or $C_{14}$ fatty acids or alkyl esters thereof in which a methylene group normally in a carbon position from 4 to 13 is replaced with oxygen or sulfur with said peptide or protein in the presence of a source of N-myristoyl transferase to thereby decrease the hydrophobicity of the resulting acyl peptide or protein compared to the corresponding myristoyl peptide or protein while maintaining about the same chain length.

* * * * *